United States Patent
Wu et al.

(10) Patent No.: US 7,682,310 B2
(45) Date of Patent: Mar. 23, 2010

(54) METHOD AND RELATED SYSTEM FOR MEASURING INTRACRANIAL PRESSURE

(75) Inventors: Chung-Yuo Wu, Taipei Hsien (TW); Yi-Hong Chou, Taipei (TW); Ta-Jung Su, Taipei Hsien (TW); Meng-Tsung Lo, Taipei Hsien (TW)

(73) Assignee: Micro-Star Int'l Co., Ltd., Jung-He, Taipei Hsien (TW)

( * ) Notice: Subject to any disclaimer, the term of this patent is extended or adjusted under 35 U.S.C. 154(b) by 379 days.

(21) Appl. No.: 11/757,413

(22) Filed: Jun. 4, 2007

(65) Prior Publication Data

US 2007/0225607 A1 Sep. 27, 2007

Related U.S. Application Data

(62) Division of application No. 10/906,709, filed on Mar. 3, 2005, now abandoned.

(51) Int. Cl.
*A61B 8/00* (2006.01)
*A61B 8/14* (2006.01)

(52) U.S. Cl. ....................... 600/438; 600/458

(58) Field of Classification Search .......... 600/438, 600/443, 455, 458; 424/9.52
See application file for complete search history.

(56) References Cited

U.S. PATENT DOCUMENTS 6,302,845 B2  10/2001  Shi et al.

FOREIGN PATENT DOCUMENTS

| JP | S59-164035 A | 9/1984 |
|----|--------------|--------|
| JP | H10-028685 | 2/1998 |
| JP | 2002-301068 A | 10/2002 |
| TW | 360524 | 6/1999 |
| WO | 01/89358 A2 | 11/2001 |
| WO | 02/43564 A2 | 6/2002 |
| WO | 2004/107963 A2 | 12/2004 |

*Primary Examiner*—Eric F Winakur
*Assistant Examiner*—Michael T Rozanski
(74) *Attorney, Agent, or Firm*—Winston Hsu

(57) ABSTRACT

A method for measuring intracranial pressure in an intracranial area filled with micro-bubbles formed by an injected contrast agent includes: (1) emitting an ultrasound signal having a bandwidth to the intracranial area, (2) receiving an echoed signal from a micro-bubble, (3) performing a spectral analysis on the echoed signal to extract a low-frequency response, which is close to a DC component, (4) calculating a resonant frequency of the micro-bubbles according to the bandwidth and strength of the low-frequency response, the bandwidth of the low-frequency response similar to the bandwidth of the ultrasound signal, (5) calculating a size of the micro-bubble according to the resonant frequency and a property of the contrast agent, and (6) calculating the intracranial pressure.

10 Claims, 5 Drawing Sheets

METHOD AND RELATED SYSTEM FOR MEASURING INTRACRANIAL PRESSURE

CROSS REFERENCE TO RELATED APPLICATIONS

This application is a division of application Ser. No. 10/906,709, filed Mar. 3, 2005, now pending.

BACKGROUND OF THE INVENTION

1. Field of the Invention

The present invention relates to a method of intracranial pressure measurement, and more particularly, to a non-invasive method of using an ultrasound contrast agent and a specific signal process for measuring intracranial pressure.

2. Description of the Prior Art

Regarding traumatic intracranial hematoma, intracranial tumor, hemorrhagic cerebrovascular disease, meningitis, or congenital cranial bone malformation, when a patient suffers from an attack of one of such diseases, intracranial pressure is usually increased. Due to meninges, blood vessels, or nerves being pressed, the patient might experience continual headaches and vomiting. What is worse, the patient might lose his vision because optic nerves can become atrophied due to optic papilla oedema. Therefore, if high intracranial pressure can be detected earlier and treatments are immediately executed, these problems can be alleviated.

Generally, references for detecting whether intracranial pressure is increased are clinical symptoms, such as headaches and vomiting. However, precise detection should be a main method for determination. There are three main detection methods as known in the prior art. One is to analyze cerebrospinal fluid extracted by lumbar puncture; another is to take an X-ray and inspect a gyri-pressure graph, bone symphysis, thickness reduction of cranium, and expansion of sella turcica, etc.; and the last is brain ultrasonic examination.

Lumbar puncture is an invasive method that has problems of infection and patient adaptation. X-ray and inspection of such are non-invasive methods, but are not efficient ways for early detection of high intracranial pressure. Ultrasonic signals used in ultrasonic examination are dramatically attenuated after traveling through the cranium, and thereby echoed signals are weak.

In recent years, in order to improve the quality of ultrasonic signals, an injection of contrast agent into blood or lymph has been used. Micro-bubbles of such a contrast agent are helpful in creating better acoustic wave feedback. Therefore, the purpose of signal improvement is achieved, which assists in measuring related parameters.

Please refer to FIG. 1, which is a frequency spectrum of ultrasound echoed signals associated with the contrast agent. As shown in FIG. 1, there are a fundamental response 11, a second harmonic response 12, and a subharmonic response 13. The latter two are non-linear and require higher emitting sound pressure to generate micro-bubbles, wherein the sound pressure required by the subharmonic response 13 is the highest.

The fundamental response 11 can be found in blood-flow and peripheral tissue, and thereby the fundamental response 11 cannot be used for comparison and recognition.

For one thing, after the second harmonic response 12 travels through the cranium, the second harmonic response 12 is dramatically attenuated due to its high frequency. Additionally, the second harmonic response 12 also occurs in mammal tissues. So it is difficult to use the second harmonic response 12 to distinguish between blood, lymph, and peripheral tissue.

A way for detecting the subharmonic response 13 is disclosed in U.S. Pat. No. 6,302,845. The patent uses a conventional ultrasound system assisted with contrast agent to estimate the pressure of the heart or portal vein. When micro-bubbles are under different pressures, differences of subharmonic responses are used for calculating the pressure accordingly. However, when the obvious subharmonic response 13 is excited by high pressure micro-bubbles can break. If the method is used for measuring intracranial pressure, micro-bubbles breaking might be a threat to the brain.

SUMMARY OF THE INVENTION

It is therefore a primary objective of the claimed invention to provide a non-invasive method and system for measuring intracranial pressure to solve the above-mentioned problem.

The claimed invention provides a method and system to measure real-time intracranial pressure.

The claimed invention also provides a precise and safe method and system to measure intracranial pressure.

The claimed invention can measure pressures of intracranial areas filled with micro-bubbles formed by a contrast agent. The system includes an ultrasound transducer, a transmitter module connected to the ultrasound transducer, a receiver module connected to the ultrasound transducer, and a signal processing module connected to the receiver module.

The method of the claimed invention includes:

(1) The transmitter module generates a driving signal to drive the ultrasound transducer to emit an ultrasound signal having a bandwidth, which is a short pulse, to the intracranial area. The attenuation of signals analyzed by the claimed invention is slight. Therefore, the ultrasound transducer can measure pressure from any intracranial areas to emit ultrasound signals traveling through cranial bones into cranial blood vessels.

(2) The ultrasound transducer senses an echoed signal from micro-bubbles and conveys the echoed signal to the receiver module.

(3) The receiver module conveys the echoed signal to the signal processing module for further processing.

(4) The signal processing module performs a spectral analysis on the echoed signal to obtain a fundamental response, a second harmonic response, a subharmonic response, and a low-frequency response. The generation of the low-frequency response can be supported by the theory and experimental results of the claimed invention. When micro-bubbles are excited by the dual-frequency acoustic signal with its two frequencies (of suitable transmission bandwidth) being close enough, a difference between the two frequencies, which is close to a DC component of the frequency spectrum (i.e., the low-frequency response) will be excited to form the low-frequency response. The low-frequency response is not excited by high pressure as the subharmonic response is, and thereby micro-bubbles will not break. Compared to the prior art, the claimed invention is safer and more suitable for measuring intracranial pressure.

(5) The signal processing module derives parameters from the bandwidth and strength of the low-frequency response so as to calculate a resonant frequency of the low-frequency response using dual-frequency analysis equations.

(6) The signal processing module calculates a micro-bubble size based on the resonant frequency and the properties of the contrast agent. Due to different contrast agents, the correlation of the sizes and the resonant frequencies is different.

(7) Finally, because surrounding pressures influence micro-bubble sizes, the signal processing module can convert micro-bubble sizes into intracranial pressures.

The claimed invention performs the calculation on the low-frequency response of the ultrasound echoed signal. The attenuation of low-frequency response traveling through cranial bones is less than that of high-frequency signals. Thus, the quality of signals received by the ultrasound transducer is better and the claimed invention can speedily and precisely calculate the pressure. In addition, the contrast agent not only can be injected into blood vessels, but also into lymph through muscles. Similarly, the claimed invention can measure pressure in areas having lymph.

Note that the low-frequency response is not excited by high pressure and has the property of low attenuation. Therefore, the claimed invention can be applied in other organs of mammals, such as the heart and portal vein. In addition, the claimed invention can be implemented in building engineering, crack detection, detecting fish in ocean, etc.

These and other objectives of the present invention will no doubt become obvious to those of ordinary skill in the art after reading the following detailed description of the preferred embodiment that is illustrated in the various figures and drawings.

DETAILED DESCRIPTION

Regarding the above description and detailed technology of the present invention, a best embodiment with drawings are disclosed as follows.

Figure 1:
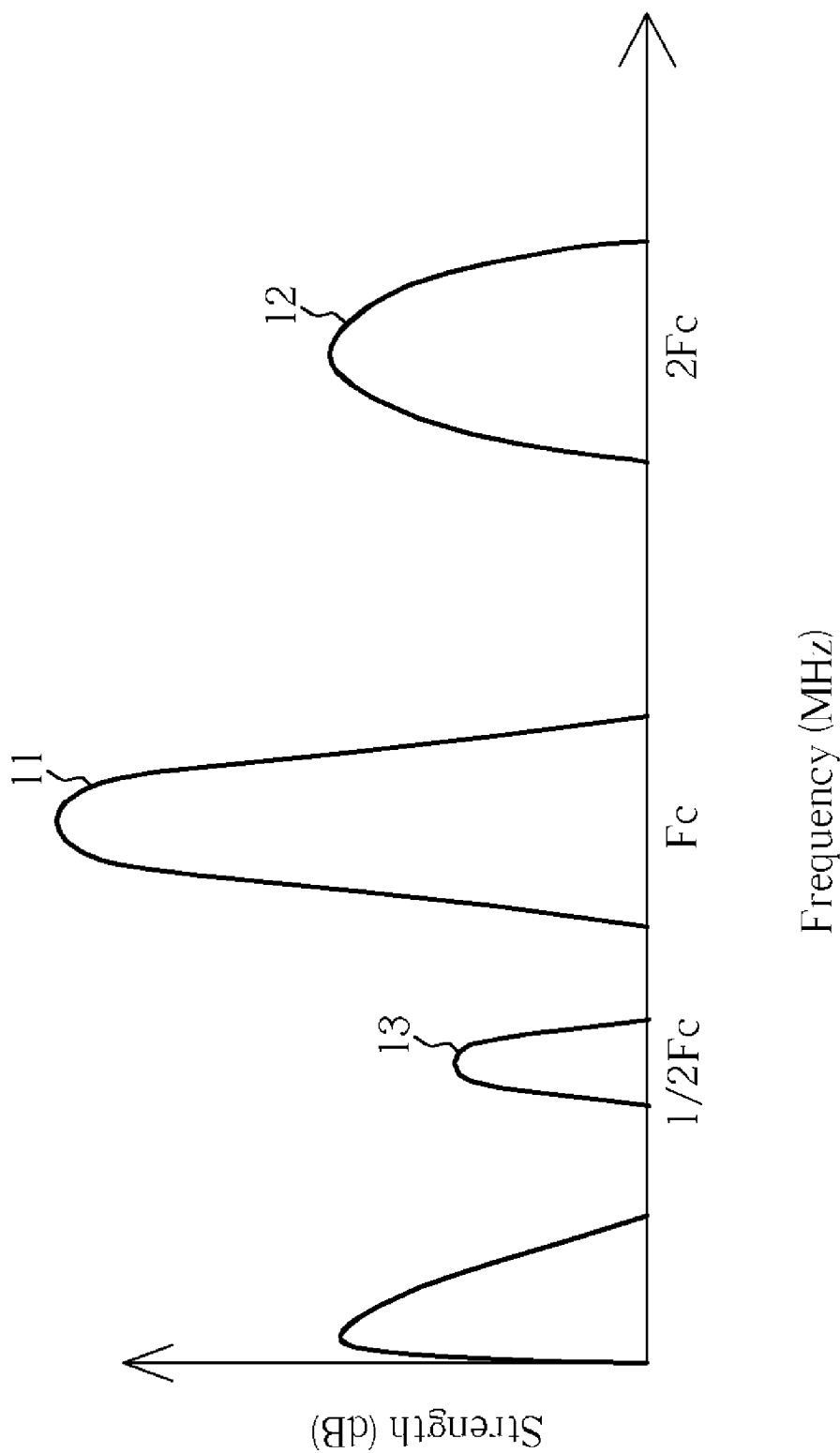
FIG. 1 is a frequency spectrum of ultrasound echoed signals associated with the contrast agent in the prior art.
Figure 2:
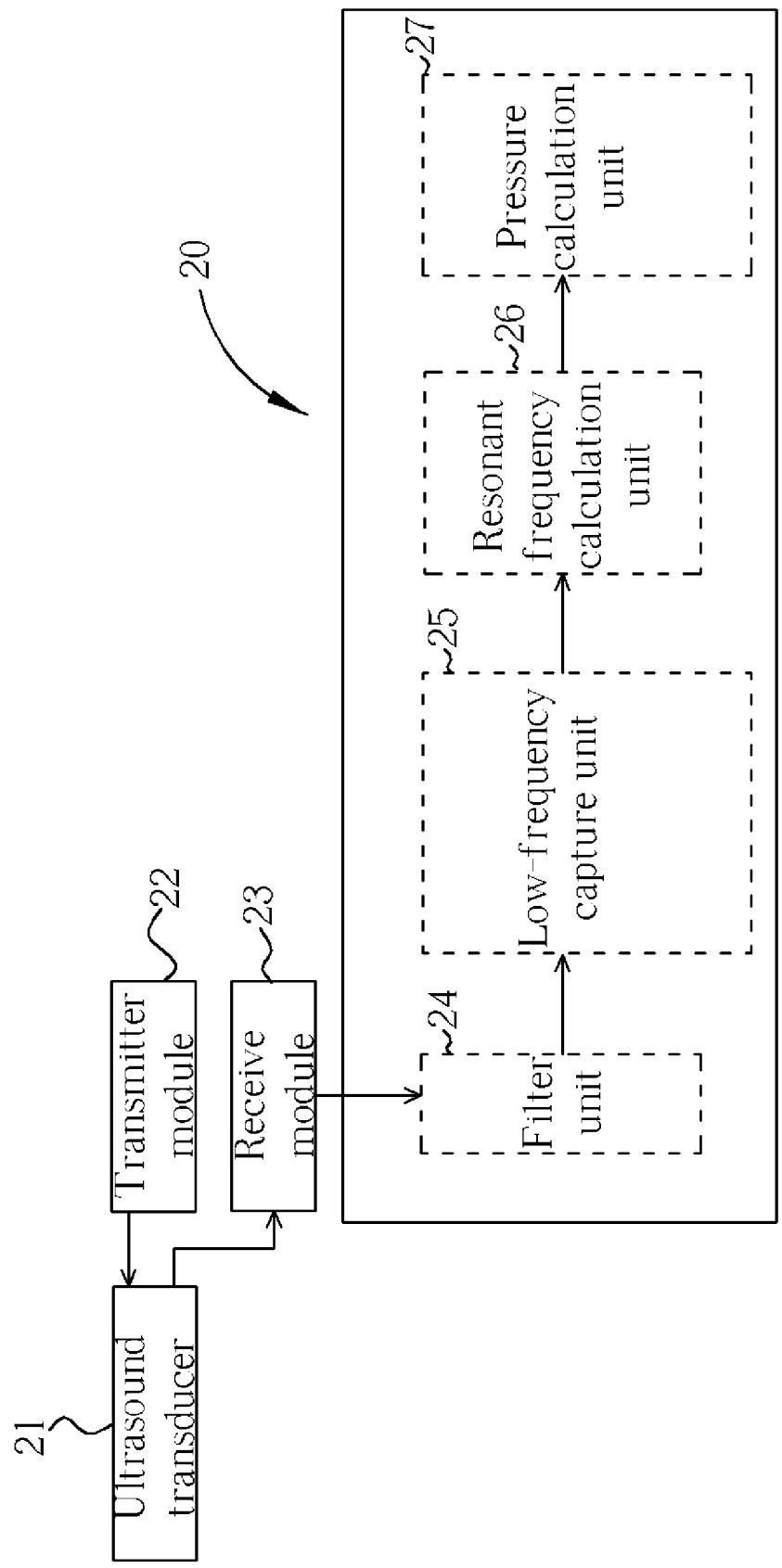
FIG. 2 is a diagram of an intracranial pressure measurement system based on the present invention.

As shown in FIG. 2, which is a diagram of an intracranial pressure measurement system based on the present invention. The best embodiment of the present invention measures a pressure of an intracranial area. The contrast agent is injected into the intracranial area by intravenous injection in advance so that blood around the area has a lot of micro-bubbles. The intracranial pressure measurement system comprises an ultrasound transducer 21, a transmitter module 22, a receiver module 23, and a signal processing module 20. The signal processing module 20 includes a filter unit 24, a low-frequency capture unit 25, a resonant frequency calculation unit 26, and a pressure calculation module 27.

Figure 3:
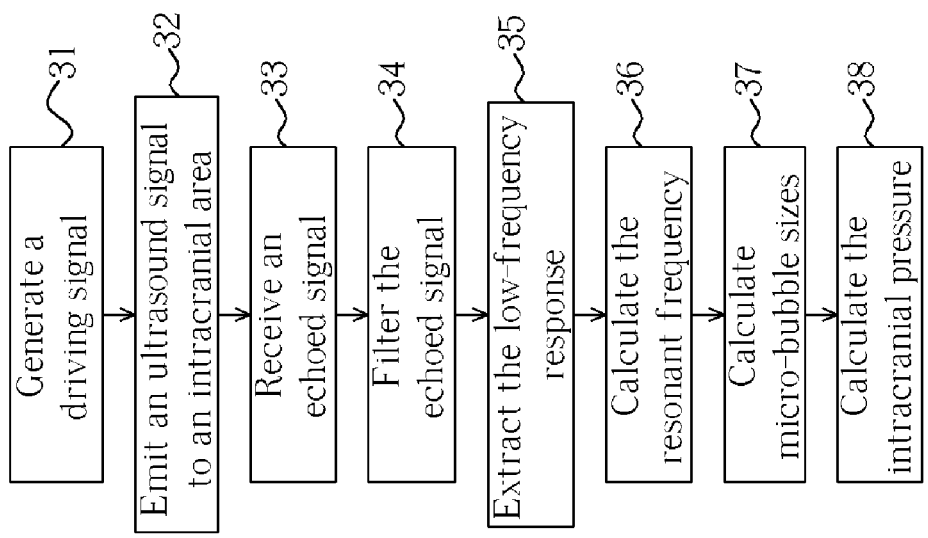
FIG. 3 is a flowchart of the intracranial pressure measurement system based on the present invention.

Please refer to FIG. 3, which is a flowchart of the intracranial pressure measurement. The steps are as follows.

Step 31: The transmitter module 22 generates a driving signal to the ultrasound transducer 21. The ultrasound transducer 21 is nestled anywhere on the patient's head in advance.

Step 32: According to the driving signal, the ultrasound transducer 21 emits an ultrasound signal having a bandwidth to travel through cranial bones to blood vessels around the intracranial area. Emitting the ultrasound signal does not require high sound pressure. The central frequency of the ultrasound signal is about 2-10 MHz generated by a typical instrument, and the bandwidth of such is about 10-40% of the central frequency. In this embodiment, the central frequency is 3.25 MHz and the bandwidth is 20% of the central frequency.

Step 33: The ultrasound transducer 21 receives an echoed signal from a micro-bubble and conveys the echoed signal to the receiver module 23.

Step 34: The receiver module 23 conveys the echoed signal to the filter unit 24 of the signal processing module 20 to filter the echoed signal so as to improve the quality of the detected echoed signal.

Figure 4:
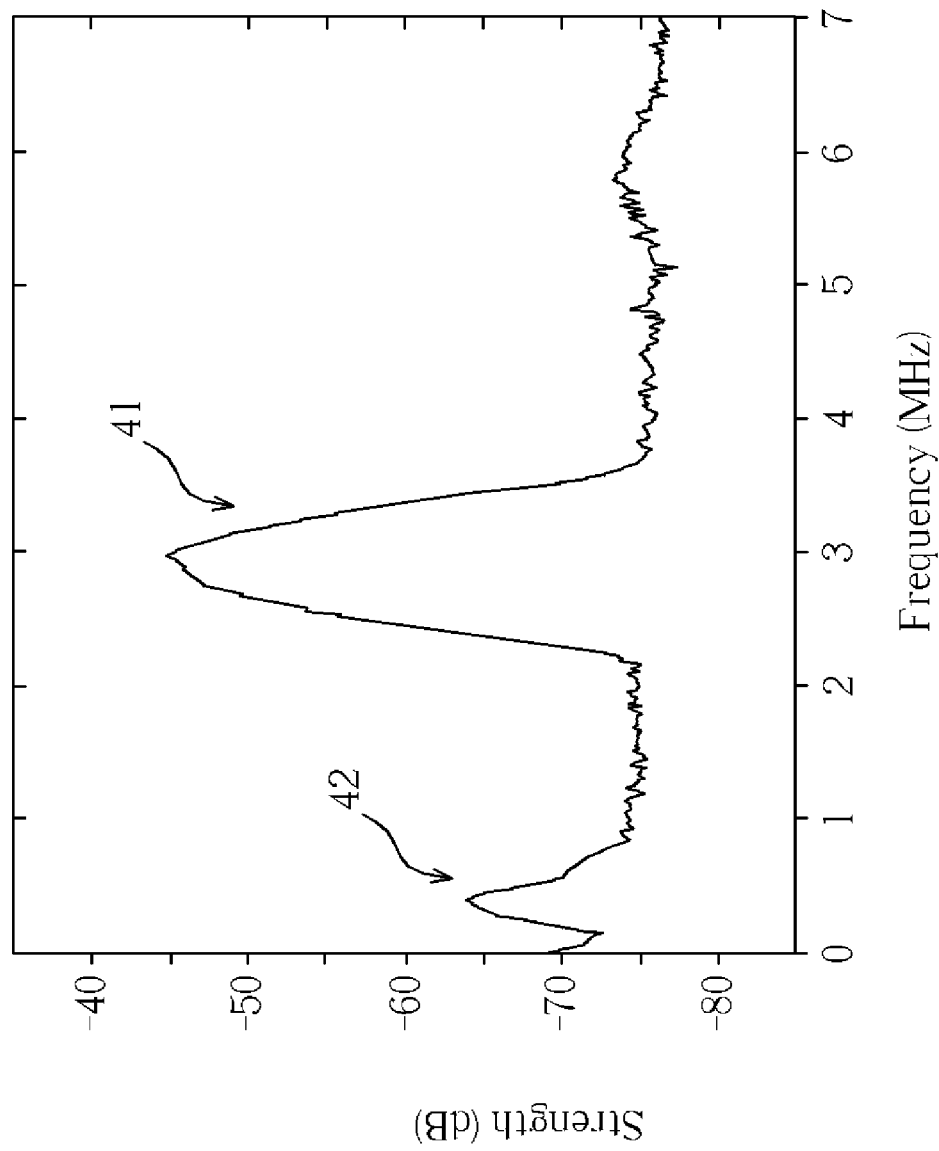
FIG. 4 is a frequency spectrum of ultrasound echoed signals according to the present invention.

Step 35: Please refer to FIG. 4, which is a frequency spectrum of ultrasound echoed signals according to the present invention. The low-frequency capture unit 25 receives the echoed signal from the filter unit 24 and performs a spectral analysis on the echoed signal. According to the frequency distribution of the echoed signal, a fundamental response 41 whose central frequency and bandwidth are quite similar to those of the ultrasound signal is obtained, and a low-frequency response 42, which is close to a DC component, is obtained. Then a band-pass filter is used to extract the low-frequency response 42. The bandwidth of the low-frequency response 42 is similar to that of the fundamental response 41.

Step 36: The resonant frequency calculation unit 26 of the signal processing module 20 takes the bandwidth and strength of the low-frequency response as parameters to calculate a resonant frequency of the low-frequency response using a dual-frequency analysis and equation 1 derived from the non-linear character of bubble resonance.

$$P^2 \propto p^2 X'^2_{12} B_e^4 \qquad \text{(equation 1)}$$

wherein P=pL/pF which is the normalization of the strength of the low-frequency response (pL is the peak value of strength of the low-frequency response, pF is the peak value of strength of the fundamental response), and p is the emitting sound pressure.

$$X'_{12} = \{[1-(\Delta f/f0)^2]^2 + [\delta \cdot \Delta f/f0]^2\}^{-1/2}$$

(f0 is the resonant frequency, Δf is the bandwidth)

Be=Δf/fc which is the normalization of the bandwidth of the fundamental response (fc is the central frequency of the fundamental response).

Figure 5:
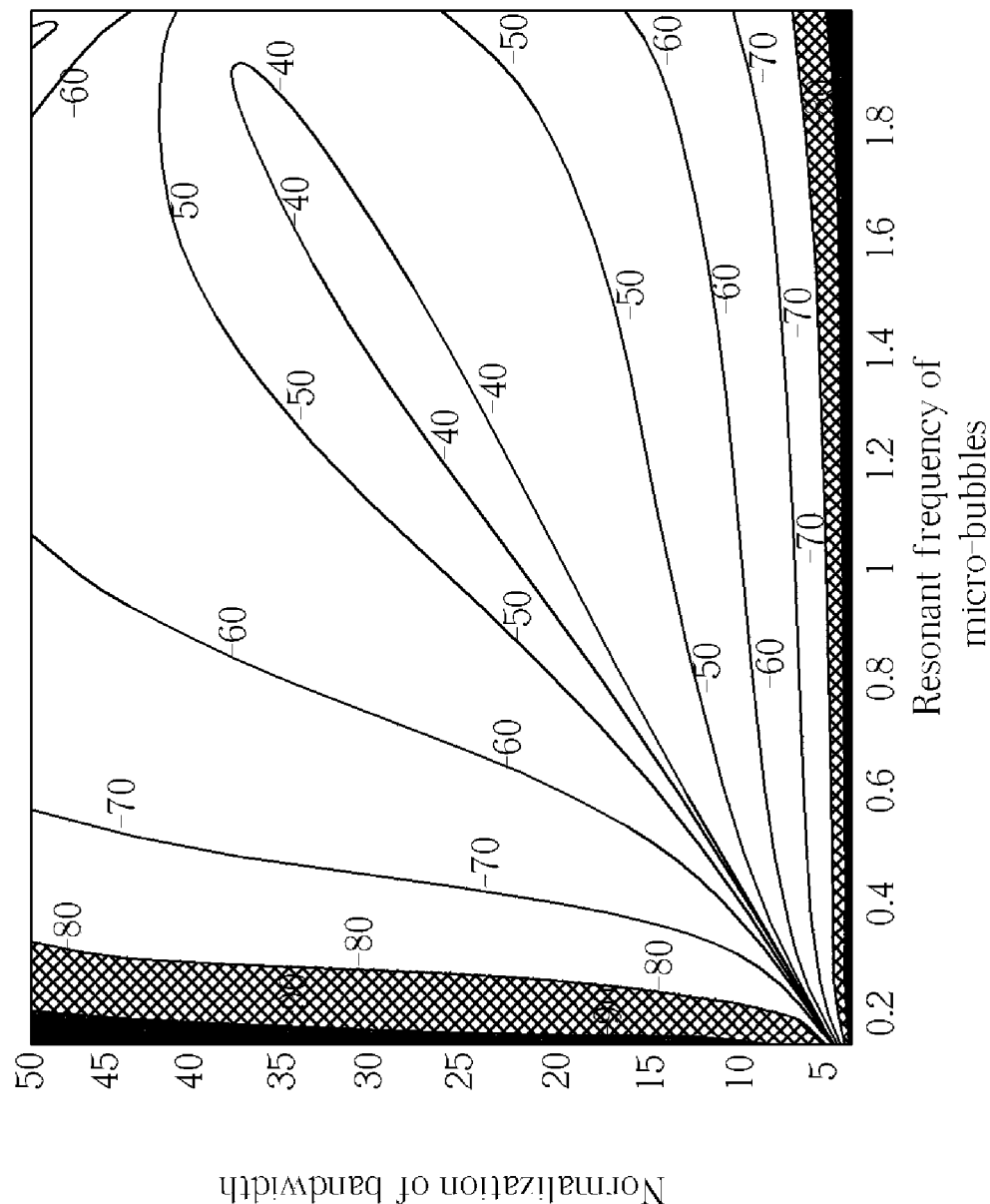
FIG. 5 is a graph of resonant frequency of micro-bubbles, and bandwidth and strength of echoed signals.

FIG. 5 is a graph of resonant frequency vs. bandwidth based on equation 1. The horizontal axis represents resonant frequency f0, its unit being MHz. The vertical axis represents normalization of bandwidth Be. The closed contour in FIG. 5 represents normalization of strength P.

The bandwidth of this embodiment is set as 20% of the central frequency. If the strength of the echoed low-frequency response 42 is obtained, the resonant frequency of micro-bubbles can be calculated from FIG. 5.

Step 37: The pressure unit 27 of the signal processing module 20 calculates the size of the micro-bubbles according to the calculated resonant frequency from step 36 and by using equation 2.

$$f0 \cdot R0 \approx 3.2 \qquad \text{(equation 2)}$$

wherein f0 represents resonant frequency, its unit being MHz, and R0 represents diameter of micro-bubble, its unit being μm.

Equation 2 is derived from the property of the contrast agent. In this embodiment, the product of a diameter and the resonant frequency of the micro-bubble is identically equal to 3.2. The product changes with different types of contrast agents.

Step 38: Finally, due to surrounding pressure's influence on micro-bubble sizes, the pressure calculation unit 27 of the signal processing module 20 converts the calculated micro-bubble size of step 37 into intracranial pressure.

To sum up, the intracranial pressure measurement system and method of the present invention have the following advantages.

(1) There is no incision required, and so no infection issue in this non-invasive measurement, and thereby it is very suitable for all kinds of patients.

(2) No other auxiliary equipment is required to use the present invention. The present invention just uses a general ultrasound system to measure the real-time pressure. Thus extra cost is reduced.

(3) In the present invention, only the low-frequency response is extracted. Since the low-frequency response suffers less attenuation because of cranial bones, the entire attenuation is governed merely by one-way (the incident path) attenuation. Therefore, the location where the ultrasound transducer 21 emits ultrasound signals and detects echoed signals can be anywhere on the head and is not limited to an eyehole (within the orbit) or the temples as the prior art is.

(4) There is no micro-bubble break issue because the echoed low-frequency response is excited by an ultrasound signal with low sound pressure. It is safer for intracranial pressure measurement.

(5) The present invention uses the low-frequency response instead of the fundamental response and the second harmonic response because it is easier to distinguish between blood and peripheral tissue. In addition, the detection depth is deeper because of the low frequency property. Compared to the subharmonic response, the low-frequency response can make sure micro-bubbles exist for a longer time and remain safe, so that they can be observed easily.

Therefore, the present invention can provide a safe, real-time, economical, and precise measurement for intracranial pressure.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of using an ultrasound contrast agent to measure pressure in an intracranial area filled with micro-bubbles formed by the injected contrast agent, the method comprising:
   (a) emitting an ultrasound signal having a bandwidth to the intracranial area;
   (b) receiving an echoed signal from a micro-bubble;
   (c) performing a spectral analysis on the echoed signal and extracting a low-frequency response, the low-frequency response formed by exciting a difference between two frequencies of a dual-frequency acoustic signal when the micro-bubbles are excited by the dual-frequency acoustic signal with the two frequencies, the difference being close to a DC component of a frequency spectrum, and the bandwidth of the low-frequency response being similar to the bandwidth of the ultrasound signal;
   (d) calculating a resonant frequency of the micro-bubble according to the low-frequency response; and
   (e) calculating a size of the micro-bubble and a pressure of the intracranial area according to the resonant frequency and a property of the contrast agent.

2. The method of claim 1 wherein step (d) comprises deriving a parameter from the bandwidth and a parameter from the strength of the low-frequency response and using an empirical equation to calculate the resonant frequency of the micro-bubble.

3. The method of claim 2 wherein the bandwidth parameter is normalized by dividing the bandwidth of the low-frequency response by a central frequency of the ultrasound signal, and the strength parameter is normalized by dividing the strength of the low-frequency response by a maximum strength of the ultrasound signal.

4. The method of claim 1 wherein step (e) comprises calculating the micro-bubble size according to a correlation between sizes of micro-bubbles and the resonant frequency of the micro-bubbles, the correlation depending on the property of the contrast agent.

5. The method of claim 4 wherein the product of the resonant frequency and a diameter of the micro-bubble is a constant value.

6. A system of using an ultrasound contrast agent to measure intracranial pressure in a target area filled with micro-bubbles formed by the injected contrast agent, the system comprising:
   a transmitter module for emitting an ultrasound signal having a bandwidth to the target area;
   a receiver module for receiving an echoed signal from a micro-bubble; and
   a signal processing module connected to the receiver module, the signal processing module comprising:
      a low-frequency capture unit for performing a spectral analysis on the echoed signal and extracting a low-frequency response, the low-frequency response formed by exciting a difference between two frequencies of a dual-frequency acoustic signal when the micro-bubbles are excited by the dual-frequency acoustic signal with the two frequencies, the difference being close to a DC component of a frequency spectrum, and the bandwidth of the low-frequency response being similar to the bandwidth of the ultrasound signal;
      a resonant frequency calculation unit for calculating a resonant frequency of the micro-bubble according to the low-frequency response; and
      a pressure calculation unit for calculating a size of the micro-bubble according to the resonant frequency and a property of the contrast agent, and further calculating an intracranial pressure of the target area.

7. The system of claim 6 wherein the resonant frequency calculation unit derives a parameter from the bandwidth and a parameter from the strength of the low-frequency response and uses an empirical equation to calculate the resonant frequency of the micro-bubble.

8. The system of claim 7 wherein the bandwidth parameter is normalized by dividing the bandwidth of the low-frequency response by a central frequency of the ultrasound signal, and the strength parameter is normalized by dividing the strength of the low-frequency response by a maximum strength of the ultrasound signal.

9. The system of claim 6 wherein the pressure calculation unit calculates the micro-bubble size according to a correlation between sizes of micro-bubbles and the resonant frequency of the micro-bubbles, the correlation depending on the property of the contrast agent.

10. The system of claim 9 wherein the product of the resonant frequency and a diameter of the micro-bubble is a constant value.

* * * * *